(12) United States Patent
Liney et al.

(10) Patent No.: US 10,391,335 B2
(45) Date of Patent: Aug. 27, 2019

(54) RADIO-FREQUENCY COIL FOR SIMULTANEOUS IMAGING AND DOSIMETRY ON AN MRI-LINAC

(71) Applicant: Ingham Institute for Applied Medical Research, Liverpool (AU)

(72) Inventors: Gary Liney, Sydney (AU); Bin Dong, Denistone East (AU)

(73) Assignee: Ingham Institute for Applied Medical Research, Liverpool, New South Wales ( * ) Notice: Subject to any disclaimer, the term of this patent is extended or adjusted under 35 U.S.C. 154(b) by 47 days.

(21) Appl. No.: 15/905,150

(22) Filed: Feb. 26, 2018

(65) Prior Publication Data

US 2018/0250527 A1 Sep. 6, 2018

Related U.S. Application Data

(60) Provisional application No. 62/466,269, filed on Mar. 2, 2017.

(51) Int. Cl.
| | |
|---|---|
| *G01V 3/00* | (2006.01) |
| *A61N 5/10* | (2006.01) |
| *G01R 33/34* | (2006.01) |
| *G01R 33/48* | (2006.01) |

(52) U.S. Cl.
CPC ..... *A61N 5/1071* (2013.01); *G01R 33/34007* (2013.01); *G01R 33/4808* (2013.01); *A61N 2005/1076* (2013.01)

(58) Field of Classification Search
USPC .......................................................... 324/309
See application file for complete search history.

(56) References Cited

U.S. PATENT DOCUMENTS

| | | | |
|---|---|---|---|
| 2015/0080704 A1* | 3/2015 | Burke | A61N 5/1049 600/411 |
| 2017/0065830 A1* | 3/2017 | Vahala | A61B 5/0555 |
| 2017/0252578 A1* | 9/2017 | Halkola | A61B 5/055 |
| 2017/0252579 A1* | 9/2017 | Kilby | A61N 5/1071 |
| 2018/0369611 A1* | 12/2018 | Owens | A61N 5/1031 |
| 2019/0054320 A1* | 2/2019 | Owens | A61N 5/1071 |

\* cited by examiner

*Primary Examiner* — Rodney E Fuller
(74) *Attorney, Agent, or Firm* — Lumen Patent Firm (57) ABSTRACT

A method of monitoring a state of a Linac beam in an MRI-Linac system for real-time in vivo patient dosimetry is provided that includes disposing a Linac beam proximal to a PIN diode of an imaging RF coil to induce RF noise in an MRI image from an MRI imager, and using the MRI imager to monitor the induced RF noise in the MRI image, where a change in a percentage of RF noise in the MRI image is used to determine a state of the Linac beam in the presence of a magnetic field of the MRI imager, where the state of the Linac beam includes an ON state, an Off state, or a relative intensity of the Linac beam.

7 Claims, 8 Drawing Sheets

FIG. 5A — low background noise

FIG. 5B — high (induced) background noise

RADIO-FREQUENCY COIL FOR SIMULTANEOUS IMAGING AND DOSIMETRY ON AN MRI-LINAC

CROSS-REFERENCE TO RELATED APPLICATIONS

This application claims priority from US Provisional Patent Application 62/466269 filed Mar. 2, 2017, which is incorporated herein by reference.

FIELD OF THE INVENTION

The present invention relates generally to radiotherapy. More particularly, the invention relates to radiotherapy that includes imaging by irradiating through radiofrequency (RF) coils.

BACKGROUND OF THE INVENTION

Radiotherapy is a form of cancer treatment that uses mega voltage x-rays from a linear accelerator to kill the tumor. Current clinical practice is to deliver the dose of radiation over a number of weeks that includes safety margins, where the dose is a compromise to between tumor kill and normal tissue toxicity. Here, no change is made to account for the individual patient during treatment, such as the response or motion of tumor etc.

An MRI-Linac is a new state-of-the art radiotherapy treatment system that combines a linear accelerator with a magnetic resonance imaging (MRI) scanner. This enables high quality images of the anatomy to be used to guide treatment in real-time offering the ability to treat tumous with greater dose and higher precision, thus improving outcomes in patients that are known to be poorly treated. Several versions of MRI-Linac are being actively pursued, marking a sea change in radiation treatment.

In vivo dosimetry is widely recognized as an effective procedure to mitigate errors in radiation therapy and is recommended for treatments involving new equipment or one-off special cases. Current methods of in vivo dosimetry are limited and cannot be used in real-time and/or in magnetic fields. Overcoming this is of vital importance in maintaining acceptable safety levels for complex and individualized treatments on an MRI-Linac.

What is needed is a method of monitoring a state of a Linac beam in an MRI-Linac system for real-time in vivo patient dosimetry in the presence of the MRI magnetic field.

SUMMARY OF THE INVENTION

To address the needs in the art, a method of monitoring a state of a Linac beam in an MRI-Linac system for real-time in vivo patient dosimetry is provided that includes disposing a Linac beam proximal to a PIN diode of an imaging RF coil to induce RF noise in an MRI image from an MRI imager, and using the MRI imager to monitor the induced RF noise in the MRI image, where a change in a percentage of RF noise in the MRI image is used to determine a state of the Linac beam in the presence of a magnetic field of the MRI imager, where the state of the Linac beam includes an ON state, an Off state, or a relative intensity of the Linac beam.

According to one aspect of the invention, a magnitude of the relative intensity of the Linac beam is calibrated prior to a treatment plan.

In another aspect of the invention, the relative intensity of the Linac beam is used to determine a treatment dose during a treatment plan.

In a further aspect of the invention, the PIN diode and the imaging RF coil are disposed at a distance d that is distal to a region of interest of a patient, where the imaging RF coil has a radius r, where $d \gg r$.

According to one aspect of the invention, a multi-leaf collimator is disposed between the Linac and a patient having a region of interest.

In a further aspect of the invention, the PIN diode includes a plurality of the PIN diodes arranged in a pattern or distributed about a region of interest in a patient under test.

In yet another embodiment of the invention, a first imaging RF coil and PIN diode combination is disposed distal to a region of interest and within a path of the Linac beam, where a second imaging RF coil and PIN diode combination is disposed proximal to the region of interest in a patient under test, where the PIN diode of the second imaging RF coil and PIN diode combination is disposed out of the Linac beam path or shielded from the Linac beam path.

DETAILED DESCRIPTION

MRI offers a number of advantages for the planning and response monitoring of radiation treated cancers. Over the last few years dedicated MRI scanners have started to become more commonplace in Oncology departments allowing the soft-tissue and functional information available from MRI to be included in the treatment plan. The desire to take this one stage further and realize real-time guidance has led to a number of groups pursuing the development of hybrid treatment systems that combine an MRI scanner with an external radiation beam. At the time of writing there are four institutions working on integrated systems either using cobalt sources or linear accelerators to provide the radiation beam. Each system has a specific range of technical challenges and solutions and a number of effects can be expected to arise from the mutual interaction between the radiation beam and the magnetic fields used to obtain the image. Among these, is the potential for the radiation beam to affect the operation and image quality of the MRI scanner through the imaging radiofrequency (RF) coil. RF receive arrays are commonly used in MRI in which a plurality of imaging RF coils are used to receive MR signal at different spatial locations in the patient's body being imaged. Typically, the receive arrays are positioned on the patient so as to maximize the signal-to-noise ratio (SNR) of the acquired signal. These coils consist of conductive loops of wire and associated electronics (e.g. matching/detuning circuit, preamplifier) which may be unavoidably placed in the path of the radiation beam. The impact of the radiation beam on MR images will depend on a number of factors including the design and arrangement of the imaging RF coil with respect to the radiation beam.

Previous work demonstrated a radiation induced current (RIC) effect in irradiated copper windings of imaging RF coils. This is believed to arise from the ejection of Compton electrons from the conductor, leading to an electronic disequilibrium and resulting in an induced current. It was shown that the presence of artefacts, and a reduction in SNR that were partly remedied by the use of build-up material. A subsequent study showed how the resulting artefacts could be removed using image post-processing. Ionizing radiation can also interfere with passive and active circuit parts, such as diodes and transistors changing their electrical characteristics as a function of beam energy resulting in induced noise. These electronic components may also show a total ionizing dose radiation damage effect due to accumulation of charge carriers at the silicon dioxide/semiconductor interfaces, which can lead to a temporal deterioration. In another study, where a radiation beam was passed through the imaging RF coil but avoided the electronic components, no ill effects were shown in a single static image. According to the current invention, no impact on the image is present when a small radiation field is directed through a large diameter integrated imaging RF coil used to receive the signal. Further, when a smaller imaging RF coil array is placed in the beam an increase in image noise is observed.

To demonstrate the effects on the imaging part of the MRI-Linac system of irradiating a target through imaging RF coils, a temporary 1.5 Tesla MRI scanner was integrated with a portable linear accelerator to enable investigation of a coupled high field inline system. A series of experiments are presented, where the imaging RF coil or imaging RF coils are placed in the path of the radiation beam to illustrate and quantify changes in performance. An elevation of the background signal was detected, which is shown to be primarily from an interaction with a PIN diode, where this effect is observable in the MRI image in real-time and fluctuated with a quantifiable dose. In an example provided herein, a pair of imaging RF coils are used to enhance the noise effect in a first instance and provide an image with minimal effect in a second instance. Signal changes that arise from the operation of imaging RF coils in the presence of a megavoltage radiation beam are presented, which are taken into account in the design of dedicated imaging RF coils for MRI-Linac systems. These signal changes enable monitoring the characteristics of the radiation beam for real-time dosimetry in the presence of the MRI magnetic field.

In one example of the invention for real-time dosimetry using MRI-Linac system, a portable industrial linear accelerator was installed next to a temporary clinical MRI scanner, which was in situ for a 10-week period. In this example, the radiation unit is capable of producing two photon beams of different energy (nominally 4 MV, and 6 MV) and two different maximum dose rates (4 Gy/min, and 8 Gy/min) corresponding to trigger rates of 200 and 400 Hz respectively. The linear accelerator is attached to a stainless-steel table with a clinical 120-leaf multi-leaf collimator (MLC) in front to provide dynamic field collimation. The whole assembly is mounted on a sliding rail system that can be used to change the source to isocentre distance (SID). The scanner is a 1.5 Tesla system operating with 40 mT/m and 200 mT/m/s gradients, 8 independent receive RF channels and a 60 cm bore diameter. The magnet was installed on blocks in order to match the beam line height.

A series of tests were performed using several standard commercial RF coils and different experimental set-ups to examine possible image effects caused by the radiation beam. The coils used were: a 4-channel flexible array; an anterior 6-channel flexible body array; a single channel 20 cm diameter loop coil; and a single channel endorectal coil. The anterior body array and the loop coil were imaged on CT in order to identify the distribution of components and in the case of the loop coil, the detuning circuit was exposed to permit further inspection of components with relation to the irradiated field. The endorectal coil had its inflatable sheath removed to allow direct irradiation of the conducting wire.

Figure 1A:
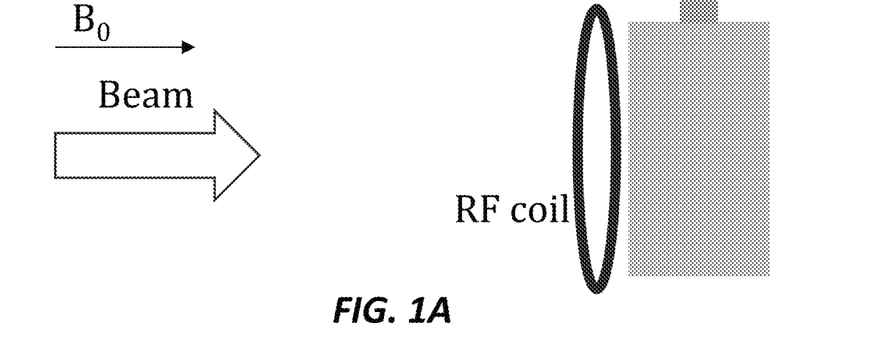
FIGS. 1A-1B show schematic diagrams to illustrate the imaging RF coil set-up used, (1A) a single imaging RF coil placed in the path of the beam and close to the phantom, (1B) a second arrangement of two coils used and positioned so that $d \gg r$, according to embodiments of the current invention.

For the majority of the tests, a phantom included a 2-liter bottle (length 24 cm x diameter 10 cm) containing water doped with $NiSO_4$ was imaged with a flexible 6-channel body coil array (30 cm×45 cm). The phantom was positioned at the isocentre with the imaging RF coil on the proximal side of the phantom in the direction of the beam as shown in FIG. 1A.

To demonstrate single beam-on image acquisition, imaging was acquired both with and without the beam turned on during the acquisition of a $T_1$-weighted spin-echo (TE/TR=22/500 ms) sequence using a 30 cm FOV, 0.8×0.6 mm resolution, 3 mm slice thickness and a receive bandwidth of 65 Hz/pixel. A reconstruction setting was changed on the system to permit the recording of the raw data as well as the magnitude DICOM data to examine effects in both k-space and image space. In each case an image was acquired and repeated using the same pre-scan settings but with the radiation beam applied. A high energy mode was used delivering a nominal 4.6 Gy to a 21×21 cm field at the isocenter (8×8 cm field size at the MLC) over the total scan duration of 3 minutes 20 seconds. Repeat measurements were made with the imaging RF coil positioned on top of the bottle (in a horizontal orientation) as well as with the imaging RF coil placed behind the phantom. In order to examine the effect of the phantom size an additional measurement was made with the RF coil placed behind three 7.3 liter test objects (37×15 cm) containing the same solution. Signal differences between the beam-ON and beam-OFF images were measured in regions-of-interest (ROI) placed within the phantom and background noise in each case.

Figure 1B:
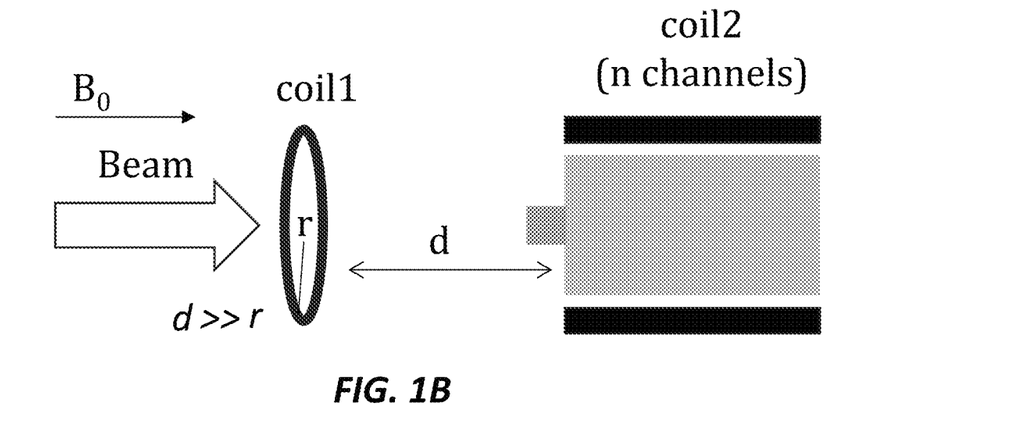
Figure 2A:
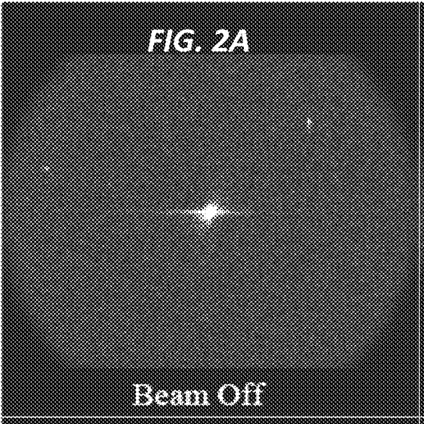
FIGS. 2A-2D show a comparison of k-space data with no beam and with the radiation beam at different energy (high/low) and trigger rate (200/400), where an interference pattern can be seen when the beam is turned on which is not present without the beam, according to embodiments of the current invention.
Figure 2B:
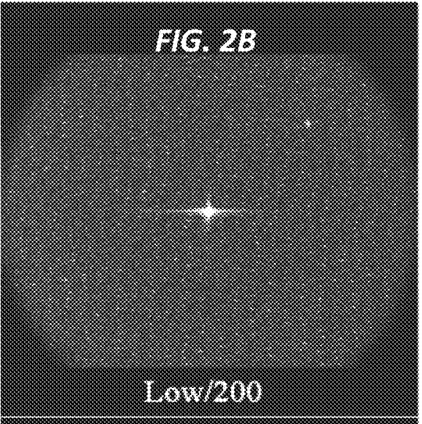
Figure 2C:
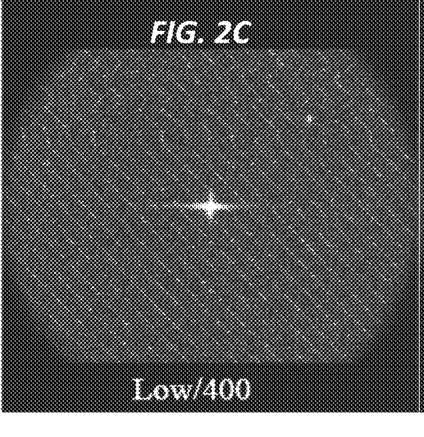
Figure 2D:
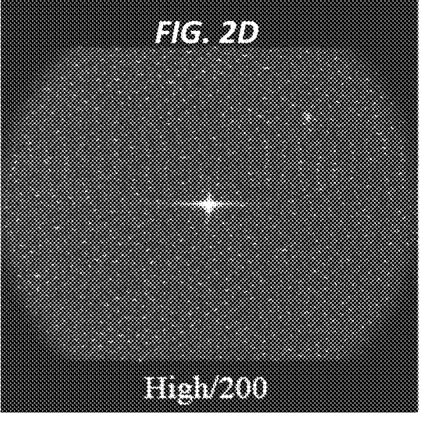

For irradiation with a dual imaging RF coil arrangement, two imaging RF coils were arranged in such a way as to separately image the noise and phantom signal (shown in FIG. 1B). A single loop surface coil (20 cm diameter) was positioned so that the beam was incident on the electronics circuit but sufficiently far enough from the phantom in order to receive no signal from the phantom. The second imaging RF coil was a 4-channel surface array, which was wrapped around the previously described test object in a conventional horizontal orientation. Measurements were obtained from a single image of all combined receiver channels (using sum of squares) as well as from separate images of the single channel from coil#1 and individual channels from imaging RF coil #2.

For the selective exposure of RF coils, in order to examine the relative interference contributions from different coil components, tests on two different RF coil designs were performed. Firstly, the endorectal coil with a conducting wire of 1.9 mm thickness was used. This coil was selected as it was the easiest to expose the conductor and its simple design meant there was no other components in the radiation field. The imaging RF coil was positioned at the magnetic isocenter so that the radiation beam was directly incident on the exposed wire.

In a second experiment the single loop coil was irradiated with varying field sizes covering the whole coil i.e. conductor (4.0 mm thickness) plus the detuning/matching circuit, and then progressively smaller areas covering parts of the electronics box. This circuit included several capacitors, inductors and a PIN diode. In each case radiosensitive film was attached to the distal side of the box and used to verify the position of the irradiated area, which was incrementally moved and reduced in size so that the beam was incident on different parts of the circuit.

Regarding the phantom contribution, the single beam-ON image test described above was also performed with the phantom removed from the magnet bore. This was carried out by first imaging with the phantom in situ in order to establish pre-scan settings (center frequency, dynamic range etc). Scans were then repeated using the same pre-scan adjustments but with the phantom no longer present, and a beam-ON and beam-OFF comparison made as before.

The beam-on image test described herein (with the RF coil in front of the phantom) was performed on a daily basis over a 5-week period as part of the machine warm-up procedure. This was to evaluate the reproducibility of the measurements and identify any possible deterioration in coil performance due to repeated irradiation during this time.

To verify dynamic imaging of a beam state, images were also acquired in a dynamic manner using a $T_1$-weighted TrueFISP sequence (TE/TR=2.2/4.4 ms, flip angle 73°, temporal resolution 0.89 s) to examine the temporal relationship with beam state for a number of different radiation beam conditions. In this case a resolution of 1.5×1.2 mm, slice thickness 3 mm and a receive bandwidth of 501 Hz/pixel was used. A total of 200 dynamic images were acquired and in the first experiment the beam was turned on with the MLC closed. In a second experiment the MLC remained fully retracted throughout, with the following changes in beam state; beam off (images 1-50); beam turned on in low energy mode and a trigger rate 200 Hz (51-100); turned off (images 101-150) and turned on again with trigger rate increased to 400 Hz (images 151-200). The signal changes were measured in the same ROIs described earlier for each image in the series.

Table 1 shows the signal variation in both the test object and background for various RF coil experiments from the static imaging tests. There was an increase in both the mean and SD of the background intensity in the reconstructed image with the radiation beam turned on. In comparison, there was negligible change in the phantom signal. The magnitude of this background effect is typically up to 16% with the smaller test object either in front or behind the coil and reduced to 5% with the coil placed horizontal to the beam direction.

The changes in the image signal are difficult to observe directly in the magnitude images. However, the artefact is more conspicuous as a regular interference pattern in the raw (k-space) data. These artefacts varied as shown in FIG. 2, with increasing dots and streaks at the higher energy or with increased trigger rate. Note that a small discrete hyperintensity can be seen, but unlike the banding pattern of the beam interference, this is present in all images.

For the dual coil arrangement it was possible to enhance the noise effect by considering the signal measured from separate receiver elements. In the overall combined image the SNR reduced slightly from 210 to 205 when the beam was turned on, and an elevation of signal (8% mean) was observed in the background intensity. When the signal channels were instead separated from respective coils it was possible to maximize the interference seen in the first coil and minimize it in the second (phantom) coil. The images from coil#2 alone demonstrated a small reduction in SNR (201 compared to 207) with only a 5% increase in background noise when the beam was turned on. No image of the phantom could be observed in coil#1, but the background noise instead increased by 30% with the beam on.

The absence of a phantom with the beam turned on produced a smaller magnitude of change compared to the same acquisition with the phantom present. This was also seen to depend on the volume of the phantom with the biggest differences noted for the larger phantom.

TABLE 1

Signal intensity values measured in images with and without (control) simultaneous radiation beam for various experimental arrangements.

| Experimental Set-up | Control | | Beam On | |
|---|---|---|---|---|
| | Phantom (mean ± SD) | Background (mean ± SD) | Phantom (mean ± SD) | Background (mean ± SD) |
| RF coil in front of phantom | 45.2 ± 4.9 | 9.5 ± 3.8 | 45.0 ± 5.6 | 11.0 ± 4.3 |
| RF coil horizontal | 127.9 | 10.7 ± 4.3 | 128.5 | 11.3 ± 4.5 |
| RF coil behind phantom | 420.2 | 28.4 ± 6.2 | 421.6 | 33.0 ± 7.2 |
| RF coil behind large phantoms | 220.9 | 36.6 ± 8.0 | 221.8 | 39.9 ± 8.6 |
| Two combined coils | 965 | 12.9 ± 4.6 | 964 | 13.9 ± 4.7 |
| coil1 only | — | 4.0 ± 2.4 | — | 5.2 ± 3.0 |
| coil2 only | 1364 | 15.9 ± 6.6 | 1367 | 16.7 ± 6.8 |
| ER coil | — | 3.9 ± 1.8 | — | 2.9 ± 1.8 |

Repeat measurements of the daily image test showed the same signal intensity changes between beam on and off (using a low dose rate) and no significant variation over time. The phantom signal (mean±SD) was 702.4±34.4 and 699.4±35.2 for beam off and beam on respectively. The corresponding background signal over the same period was 30.2±0.2 and 32.4±0.3 for beam off and beam on.

Figure 3:
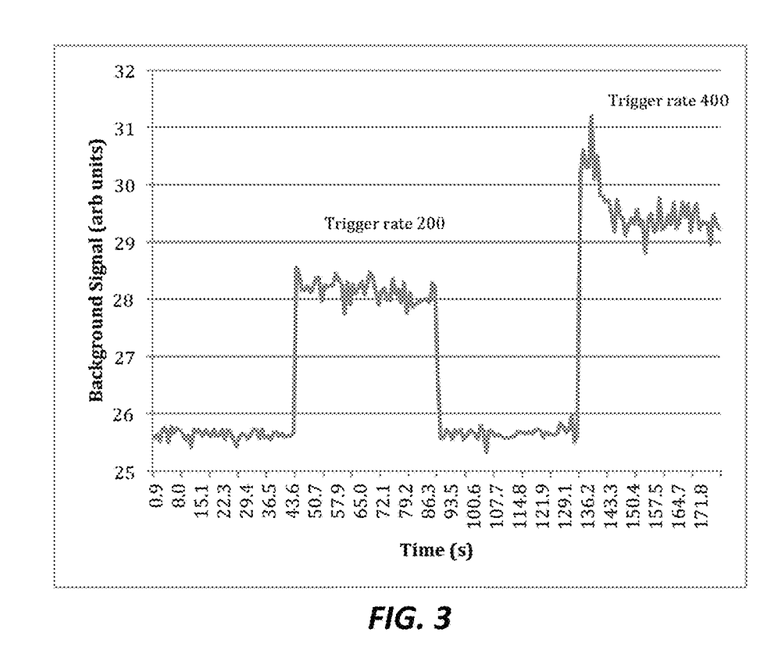
FIG. 3 shows a plot of background signal intensity versus time with the MLC retracted and two different beam-on durations using a low energy mode and two different dose (trigger) rates of 200 and 400 Hz, according to embodiments of the current invention.

Results from the dynamic image acquisitions demonstrated the same characteristic noise elevation with beam on but at an increased magnitude. Using the same surface coil arrangement, an elevation of background intensity of up to 25% was observed with a negligible change in phantom signal. No change was observed when the linear accelerator was in operation but with the MLC closed. This showed that the RF effect was caused by the irradiation directly and not any extraneous noise from the accelerator, which is outside the RF cage. FIG. 3 shows changes in background signal for the two different dose (trigger) rates. Initially the low energy-low dose rate produces approximately 10% increase in background intensity. The second beam on period, at the higher dose rate of 400, produced a 15% increase in background signal. There was an initial overshoot in response which can be attributed to the relative instability of this type of industrial radiation device which was frequently noted when changing between energy modes. The signal can be seen to return to the baseline value in between the two beam-on periods.

When the endorectal coil conducting wire was irradiated directly no difference could be detected between the beam on and beam off image acquisition. Selective irradiation of the larger loop coil demonstrated that the principle source of the noise increase was from within the electronics circuit and this was further isolated as being the PIN diode; there was no concomitant change in effect when either the conducting wire or other components were also included in the irradiated area. In one aspect of the invention, a detuning/matching circuit in the single loop coil and piece of Gafchromic film used in the procedure of selectively irradiating this coil was provided. The PIN diode is proximal to other components, such as three capacitors, and two inductors.

According to one embodiment, to maximize SNR on any MR-Linac system, the invention uses coils of much smaller size, leading to the likelihood of the radiation beam impinging on these coils or some components thereof, such as the PIN diode. Described herein is how an interference effect can be seen within the image, and that the principal cause was attributed to irradiation of a PIN diode.

Described herein is an elevation of signal in the background of the magnitude image with beam-on of up to 30% with a negligible change in the primary image signal. This reduces SNR in the image but if this is sufficiently high then the effect is used advantageously to monitor beam state. The effect is highly reproducible, synchronous with the beam and varied with energy and dose rate. An increased effect was seen in the dynamic image sequence which used a very short repetition time (TR) and a high receive bandwidth; both of which impact of a fast-pulsed radiation beam in a low SNR acquisition. The presence of the phantom also increased the magnitude of the effect presumably due to the contribution from back scattered irradiation.

A radiation induced current from the metal conductor of the coil conductor is generally not observed. This could be due to the differences in radiation dose, experimental set-up but also the amount of conductor being irradiated.

By selectively irradiating sub-sections of the loop coil the dominant effect is identified as being interference in the PIN diode(s) and this is likely to surpass any RIC effect that may arise from the conductor. For a PIN diode, the real-time effect of the interaction with the radiation beam is generation of a photocurrent due to Frenkel pairs generated by secondary electrons interacting with the silicon lattice. The excess of carriers generated in the substrate drifts towards the electrodes varying instantaneously the effective operating point of the device in the circuit. This effect generates oscillations of the output signal of the detuning/matching circuit leading to an increase of the noise, which disappears when the beam is off. In the larger phased-array coil, with diodes at each coil element location, the effect change is seen with increasing MLC size, which can be attributed to the irradiation of an increasing number of involved components. The conducting path in this coil was subsequently determined to be copper strips of only 0.4 mm thickness, so RIC can be assumed to be a negligible contribution.

Although diodes can take considerable amounts of radiation, accumulated radiation damage can change the magnitude of the effect over a longer period. However, we found no deterioration of coil performance over the timescale studied suggesting the absence of a radiation damage mechanism. According to a further aspect of the invention, the diode arrays are pre-irradiated to stabilize their subsequent sensitivity.

Figure 4:
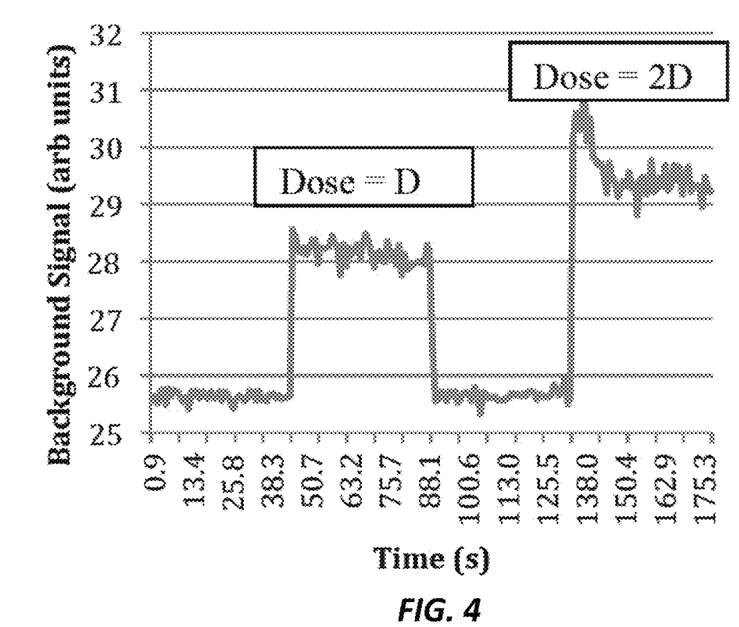
FIG. 4 shows a plot of the response in the imaging RF coil scales with dose meaning it can be calibrated to produce in vivo dosimetry, according to embodiments of the current invention.

In yet another aspect, the invention has a cross-over applications into MRI, since the invention provides radiation interference as an integral part of the imaging system in one or several receiver channels. The current invention provides efficient and real-time patient dosimetry disposed to harness MRI-Linac technology and deliver higher doses to moving targets with sub millimeter precision. Here, the change in noise indicates the beam state in the presence of a magnetic field during a dynamic scan while maintaining sufficient SNR in the imaged object. This variation with dose rate is then used for in vivo dosimetry, where the RF coils are specifically designed for MR-Linac so they actively incorporate and utilize radiation induced changes as part of the image acquisition. The beam status of the radiation from the real-time image is used to guide the treatment. The RF noise produced within an MRI image is relatively small and uniformly spread throughout the background of the image, which generally has no negative effect on the image guidance. The induced RF noise in the MRI image scales with the radiation dose to provide real-time dosimetry during a treatment plan, and delivery of higher doses to moving targets with sub millimeter precision. FIG. 4 shows the background noise effect scales with radiation dose and the effect is immediate resulting in real-time dosimetry.

Figure 5A:
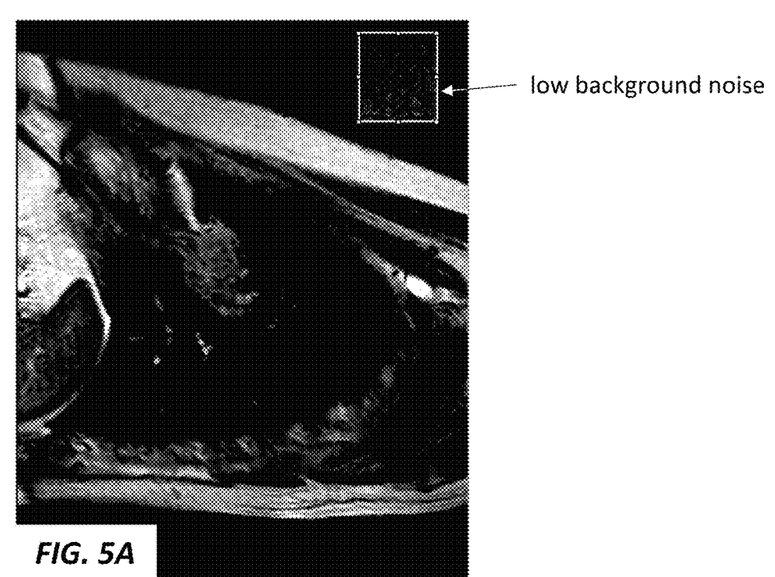
FIGS. 5A-5B show the noise in MRI images that is highlighted in the corner box- it is increased in the image of FIG. 5B, e.g. due to radiation hitting the imaging coil; there is little effect on the image but it can be used in real time (5B) to show when the radiation is activated- ensuring safety, according to one embodiment of the invention.
Figure 5B:
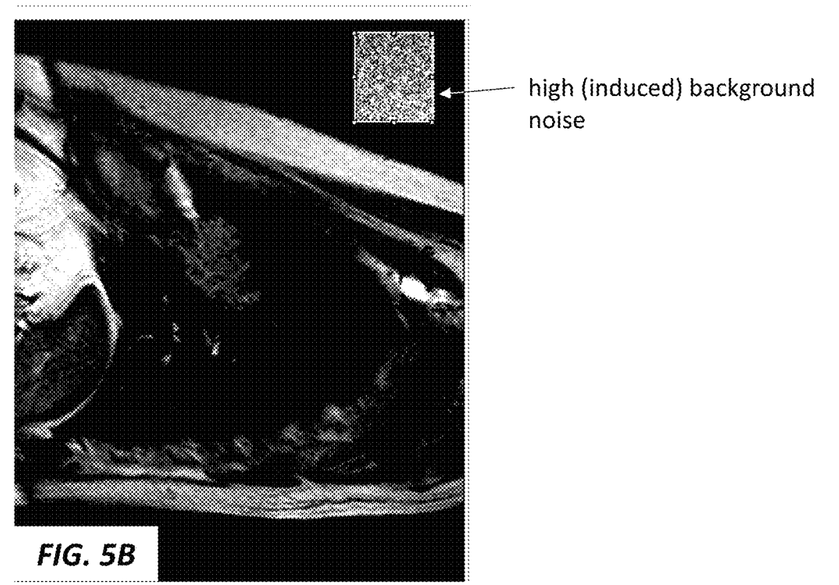

FIGS. 5A-5B show the noise in MRI images that is highlighted in the corner boxes, where in FIG. 5A, the corner box shows relatively low background noise, and in FIG. 5B the induced background noise is shown increased due to radiation hitting the PIN diode of the MRI imaging coil. It is shown that there is little effect on the image, but the induced background noise is used for real-time dosimetry in FIG. 5B, and also to show when the radiation is activated- ensuring safety, according to one embodiment of the invention.

Figure 6A:
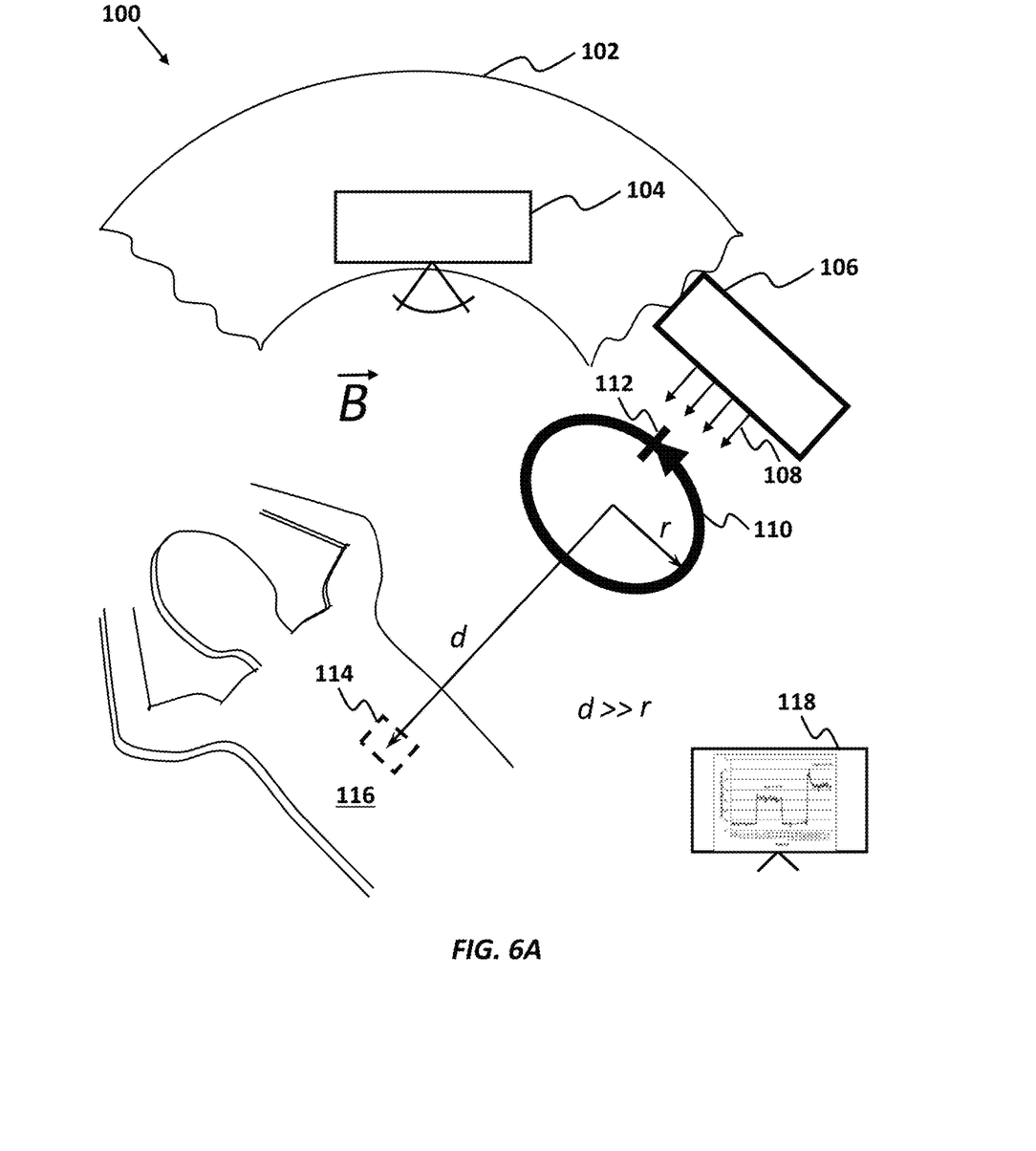
FIGS. 6A-6D show schematic drawings of the real-time MRI-Linac dosimetry system setup that includes (6A) the imaging RF coil and PIN diode with $d \gg r$, (6B) the imaging RF coil and PIN diode placed proximal to the region of interest, (6C) a pattern or distribution of imaging RF coils and PIN diodes place proximal to one or more regions of interest, (6D) the imaging RF coil and PIN diode with $d \gg r$, and) the imaging RF coil placed proximal to the region of interest with and PIN diode outside the beam path or shielded from the beam, according to embodiments of the invention.

The RF coil can be made of separate active components that produce dose and spatial information at any given moment during treatment. FIGS. 6A-6D show schematic drawing of the real-time MRI-Linac dosimetry system 100 setup. FIG. 6A shows an Mill magnetic 102 and MRI imager 104 combined with a Linac 106 x-ray source directing a treatment beam 108 in the presence of the MRI magnetic field (B). Further shown is a single Imaging RF coil 110 having a PIN diode 112 disposed within the path of the treatment beam 108 and above the region of interest (ROI) 114 of a patient 116. In this example, the distance (r) from the ROI 114 to the Imaging RF coil 110 and PIN diode 112 is much greater than the diameter (d) of the imaging RF coil 110 (d>>r). The condition of the status of the treatment beam 108 is output to a computer/display 118.

Figure 6B:
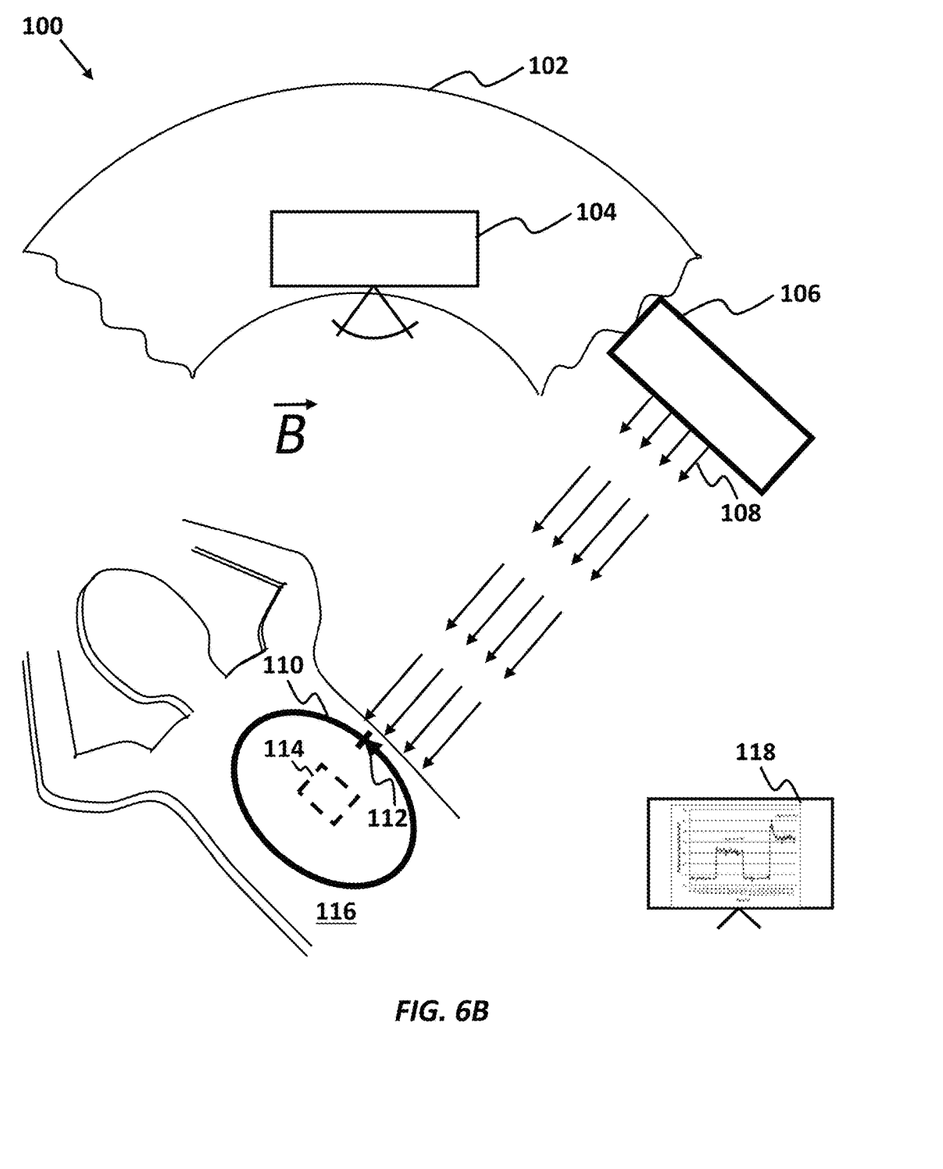

FIG. 6B shows another schematic drawing of the real-time MRI-Linac dosimetry system 100 setup, according to one embodiment of the invention, where a single imaging RF coil 110 having a PIN diode 112 disposed within the path of the treatment beam 108 is proximal to, about, or on the region of interest (ROI) 114 of the patient 116.

Figure 6C:
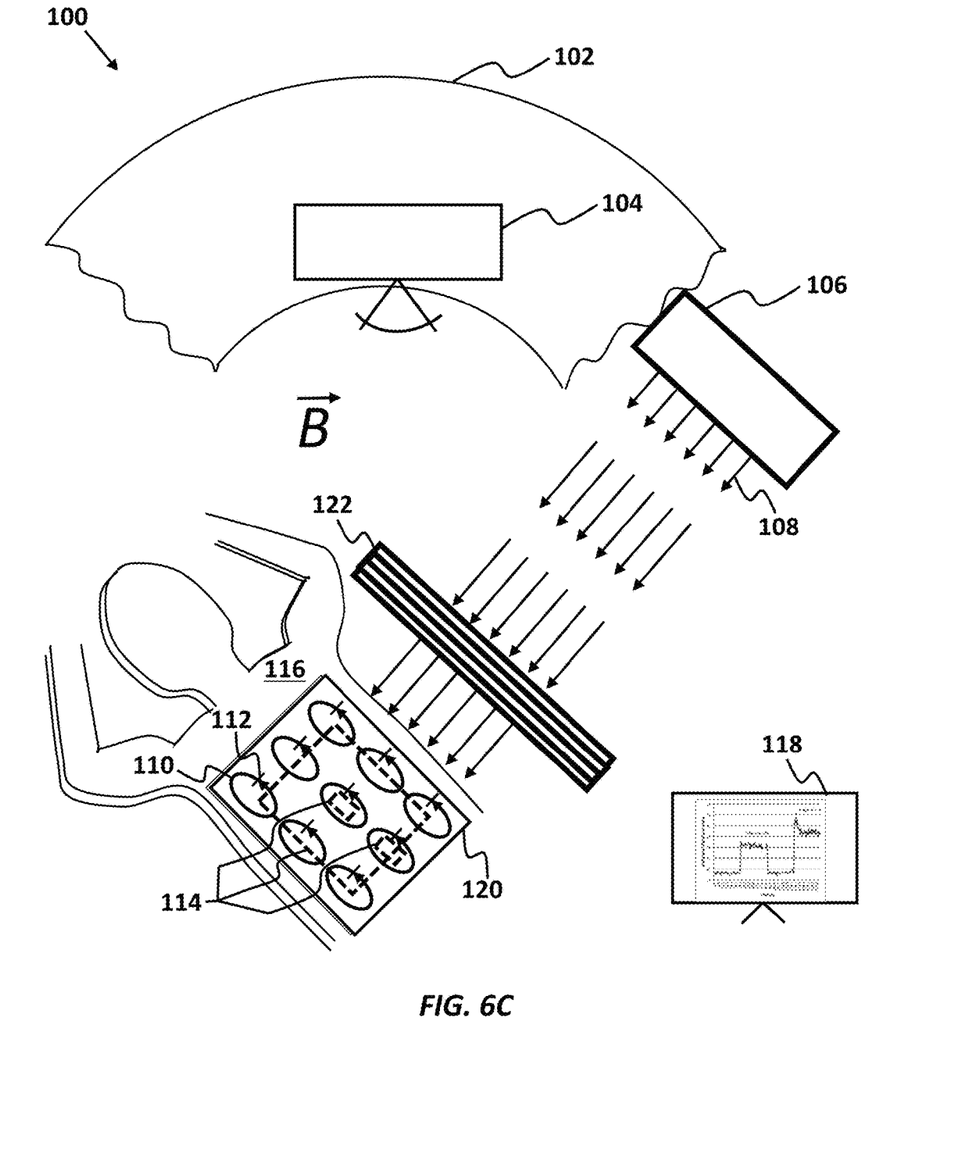

FIG. 6C shows a further schematic drawing of the real-time MRI-Linac dosimetry system 100 setup, according to further embodiment of the invention, where sensor sheet 120 that holds a pattern, array, or a distribution of the imaging RF coils 112 and PIN diodes 110 are place proximal to one or more ROI's 114. FIG. 6C further shows a multi-leaf collimator (MLC) 122 disposed between the Linac 106 x-ray source and imaging RF coils 112 and PIN diodes 110, where real-time dosimetry is enabled during a dynamic treatment plan that includes scanning a single ROI 114, multiple ROI's 114, or a relative larger distribution of ROI's 114, according to further embodiments of the invention.

Figure 6D:
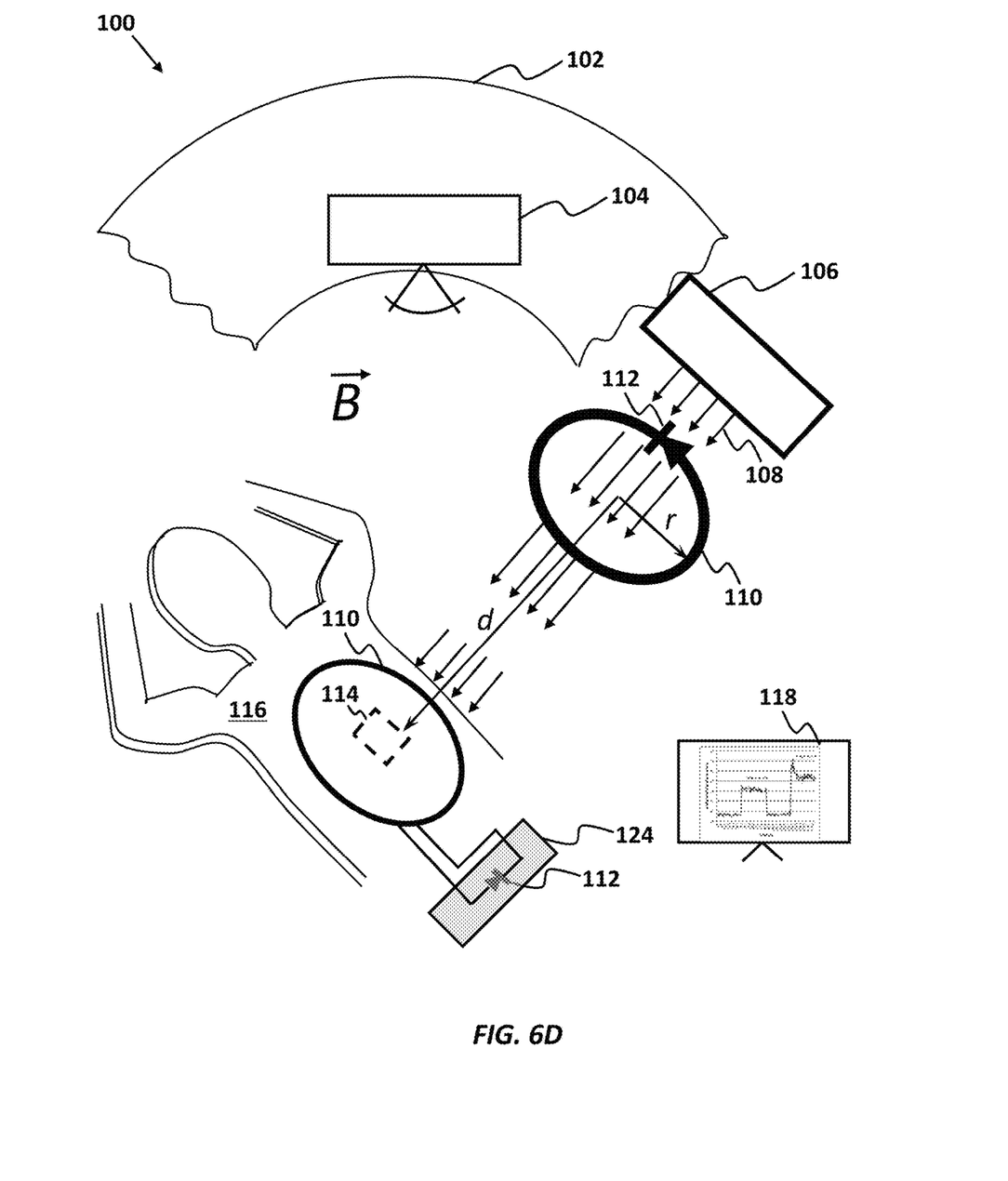

FIG. 6D shows another schematic drawing of the real-time MRI-Linac dosimetry system 100 setup, according to further embodiment of the invention, having the MRI magnetic 102 and MRI imager 104 combined with a Linac 106 x-ray source directing a treatment beam 108 in the presence of the MRI magnetic field ($\vec{B}$). Further shown is the single Imaging RF coil 110 with the PIN diode 112 disposed within the path of the treatment beam 108 and above the region of interest (ROI) 114 of a patient 116. In this example, the distance (r) from the ROI 114 to the imaging RF coil 110 and PIN diode 112 is much greater than the diameter (d) of the Imaging RF coil 110 ($d \gg r$). The condition of the status of the treatment beam 108 is output to a computer/display 118. Further shown is another imaging RF coil 110 disposed within the path of the treatment beam 108 and is proximal to, about, or on the region of interest (ROI) 114 of the patient 116, however the PIN diode 112 is outside the path of the beam 108 or shielded 124 from the beam 108, according one embodiment of the invention. Here, the use of the two imaging RF coils 110, one of which is approximately half way between the Linac 108 and the ROI 114 ($d \gg r$) having the imaging RF coil 110 and PIN diode 112 within the path of the beam 108, as shown in FIG. 6A, and the other coil 110 configured according to the setup shown in FIG. 6B except the PIN diode is out of the path of the beam 208, or shielded 124 from the beam 108, such that the setup shown in FIG. 6D enables one imaging RF coil to act as a dose receiver (as shown in FIG. 6A with $d \gg r$) and the second Imaging RF coil to act as the imaging coil only as shown in FIG. 6B. According to one variation of the current embodiment, the second imaging RF coil 110 is close to the patient 116 but aligned in another orientation, where the imaging RF coil 110 that is proximal to the patient 116 is still sensitive to the image but not to the RF noise-effectively, and two imaging RF coils 112 are optimized for their individual roles of dose versus imaging.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A method of monitoring a state of a Linac beam in an MRI-Linac system for real-time in vivo patient dosimetry, comprising;
    a) disposing a Linac beam proximal to a PIN diode of an imaging RF coil to induce RF noise in an MRI image from an MRI imager; and
    b) using said MRI imager to monitor said induced RF noise in said MRI image, wherein a change in a percentage of RF noise in said MRI image is used to determine a state of said Linac beam in the presence of a magnetic field of said MRI imager, wherein said state of said Linac beam comprises an ON state, an Off state, or a relative intensity of said Linac beam.

2. The method according to claim 1, wherein a magnitude of said relative intensity of said Linac beam is calibrated prior to a treatment plan.

3. The method according to claim 1, wherein said relative intensity of said Linac beam is used to determine a treatment dose during a treatment plan.

4. The method according to claim 1, wherein said PIN diode and said imaging RF coil are disposed at a distance d that is distal to a region of interest of a patient, wherein said imaging RF coil comprises a radius r, wherein $d \gg r$.

5. The method according to claim 1, wherein a multi-leaf collimator is disposed between said Linac and a patient having a region of interest.

6. The method according to claim 1, wherein said PIN diode comprises a plurality of said PIN diodes arranged in a pattern or distributed about a region of interest in a patient under test.

7. The method according to claim 1, wherein a first imaging RF coil and PIN diode combination is disposed distal to a region of interest of a patient under test and within a path of said Linac beam, wherein a second said imaging RF coil and PIN diode combination is disposed said region of interest of said patient under test, wherein said PIN diode of said second imaging RF coil and PIN diode combination is disposed out of said Linac beam path or shielded from said Linac beam path.

* * * * *